US00PP18863P2

(12) United States Plant Patent
Trees

(10) Patent No.: US PP18,863 P2
(45) Date of Patent: Jun. 3, 2008

(54) ***GERANIUM* PLANT NAMED 'BALDESLIPZLE'**

(50) Latin Name: *Pelargonium ×hybrida*
Varietal Denomination: Baldeslipzle

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 74 days.

(21) Appl. No.: 11/605,154

(22) Filed: Nov. 28, 2006

(51) Int. Cl.
*A01H 5/00* (2006.01)

(52) U.S. Cl. ..... Plt./324

(58) Field of Classification Search ..... Plt./324
See application file for complete search history.

*Primary Examiner*—Annette H Para
(74) *Attorney, Agent, or Firm*—Audrey Charles

(57) ABSTRACT

A new and distinct cultivar of *Geranium* plant named 'Baldeslipzle', characterized by its semi-double type dark pink and white bicolored flowers, medium green-colored foliage, and moderately vigorous, upright growth habit.

1 Drawing Sheet

Latin name of genus and species of plant claimed: *Pelargonium×hybrida.*
Variety denomination: 'Baldeslipzle'.

BACKGROUND OF THE INVENTION

The present invention relates to a new and distinct cultivar of *Geranium* plant botanically known as *Pelargonium× hybrida* and hereinafter referred to by the cultivar name 'Baldeslipzle'.

The new cultivar originated in a controlled breeding program during June 2003 at Arroyo Grande, Calif. The objective of the breeding program was the development of *Geranium* cultivars that flower uniformly with attractive flower and foliage coloration and a medium vigorous, upright growth habit.

The new *Geranium* cultivar is the result of cross-pollination. The female (seed) parent of the new cultivar is Rocky Mountain Scarlet 'Fislet', U.S. Plant Pat. No. 12,453, characterized by its semi-double type scarlet red-colored flowers, medium green-colored foliage with strong zonation, and upright growth habit. The male (pollen) parent of the new cultivar is Designer Cherry 'Baldescher', U.S. Plant Pat. No. 13,998, characterized by its semi-double type cherry red-colored flowers, medium green-colored foliage, and upright growth habit. The new cultivar was discovered and selected as a single flowering plant within the progeny of the above stated cross-pollination during May 2004 in a controlled environment at Arroyo Grande, Calif.

Asexual reproduction of the new cultivar by terminal stem cuttings since May 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baldeslipzle' as a new and distinct cultivar of *Geranium* plant:

1. Semi-double type dark pink and white bicolored flowers;
2. Medium green-colored foliage; and
3. Moderately vigorous, upright growth habit.

Plants of the new cultivar differ from plants of the female parent primarily in flower color and from plants of the male parent primarily in flower color.

Of the many commercially available *Geranium* cultivars known to the inventor, the most similar in comparison to the new cultivar is Fantasia® Strawberry Sizzle 'Sil Claudio', not patented. However, in side by side comparisons, plants of the new cultivar differ from plants of 'Sil Claudio' in the following characteristics:

1. Plants of the new cultivar are shorter and wider than plants of 'Sil Claudio'; and
2. Plants of the new cultivar have a flower color different from plants of 'Sil Claudio'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldeslipzle'. The plants were grown in 4.5 inch pots for 8 weeks in a greenhouse at West Chicago, Ill.

DETAILED BOTANICAL DESCRIPTION

Figure 1:
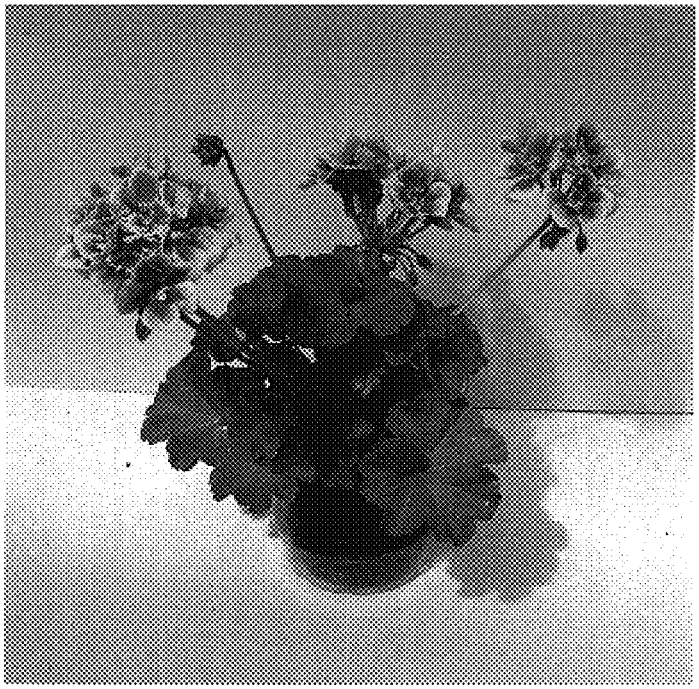
FIG. 1 illustrates a side view of the overall growth and flowering habit of 'Baldeslipzle'.
Figure 2:
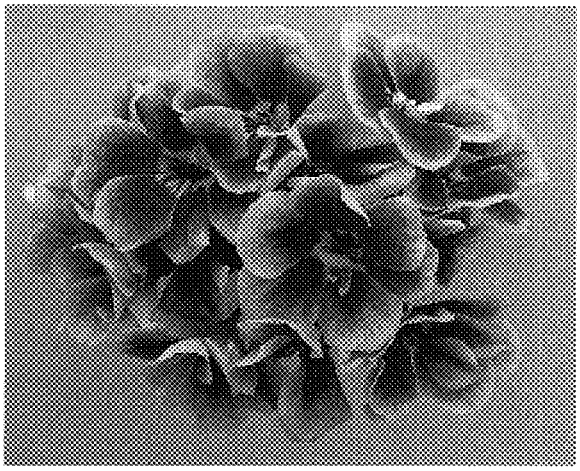
FIG. 2 illustrates a close-up view of an individual umbel of 'Baldeslipzle'.
Figure 3:
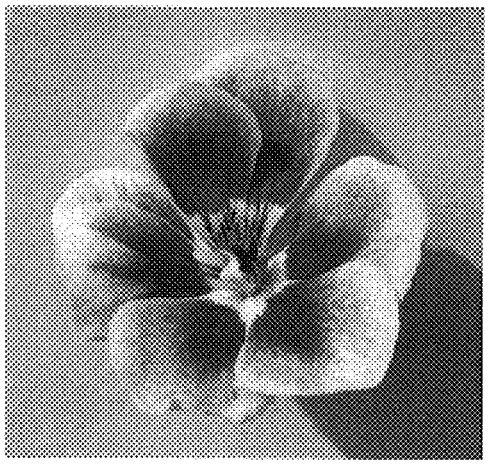
FIG. 3 illustrates a close-up view of an individual flower of 'Baldeslipzle'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 21, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Pelargonium×hybrida* cultivar Baldeslipzle.

Parentage:

*Female parent.*—'Fislet', U.S. Plant Pat. No. 12,453.

*Male parent.*—'Baldescher', U.S. Plant Pat. No. 13,998.

Propagation:

*Type cutting.*—Terminal stem.

*Time to initiate roots.*—Approximately 9 to 13 days.

*Time to produce a rooted cutting.*—Approximately 18 to 20 days.

*Root description.*—Fibrous.

*Rooting habit.*—Freely branching.

Plant description:

*Commercial crop time.*—Approximately 8 to 9 weeks from a rooted cutting.

*Growth habit and general appearance.*—Moderately vigorous, upright.

*Size.*—Height from soil level to top of plant plane: Approximately 20.6 cm. Height from soil level to top of foliage: Approximately 10.4 cm. Width: Approximately 29.1 cm.

*Branching habit.*—Freely basal branching. Quantity of main branches per plant: Approximately 3.

*Branch.*—Strength: Strong. Length: Approximately 4.7 cm. Diameter: Approximately 6.4 mm. Length of central internode: Approximately 8.4 mm. Texture: Densely pubescent with a mixture of glandular and nonglandular hairs. Gland color: Mixture of colorless, transparent; and 29C, transparent. Color of young and mature stems: 144A.

Foliage description:

*General description.*—Quantity of leaves per lateral branch: Approximately 10. Fragrance: None. Form: Simple. Arrangement: Opposite.

*Leaves.*—Aspect: Petiole is at an acute angle to stem and blade is perpendicular to stem. Shape: Reniform. Margin: Crenate, palmately lobed. Apex: Obtuse. Base: Cordate. Venation pattern: Palmate. Length of mature leaf: Approximately 5.0 cm. Width of mature leaf: Approximately 8.3 cm. Texture of upper surface: Densely pubescent with a mixture of glandular and nonglandular hairs. Texture of lower surface: Pubescent with a mixture of glandular and nonglandular hairs, dense on venation. Gland color: Colorless, transparent. Color of upper surface of young foliage: 137B with venation of 137A. Color of lower surface of young foliage: 137C with venation of 146C. Color of upper surface of mature foliage: 137A with venation of 137A. Color of lower surface of mature foliage: 137C with venation of 144A.

*Petiole.*—Length: Approximately 6.0 cm. Diameter: Approximately 2.0 mm. Texture: Densely pubescent with a mixture of glandular and nonglandular hairs. Gland color: Mixture of colorless, transparent; and 29C, transparent. Color: 144A.

Flowering description:

*Flowering habit.*—'Baldeslipzle' is freely flowering under outdoor growing conditions with substantially continuous blooming from spring through autumn and year-round in greenhouse environment.

*Lastingness of individual flower on the plant.*—Approximately 13 to 15 days.

Inflorescence description:

*General description.*—Type: Umbel. Positioned above foliage. Quantity of fully open umbels per plant: Approximately 3. Quantity of developing umbels per plant: Approximately: 3. Fragrance: None. Length or height: Approximately 5.9 cm. Width: Approximately 10.6 cm. Quantity of fully open flowers per inflorescence: Approximately 15.

*Peduncle.*—Strength: Strong. Aspect: Erect. Length: Approximately 14.7 cm. Diameter: Approximately 3.5 mm. Texture: Densely pubescent with a mixture of glandular and nonglandular hairs. Gland color: Mixture of colorless, transparent; and 29C, transparent. Color: 144A.

Flower description:

*General description.*—Type: Semi-double.

*Bud.*—Rate of opening: Generally takes 3 to 5 days for bud to progress from first color to fully open flower.

*Bud just before opening.*—Shape: Elliptic. Length: Approximately 1.6 cm. Width: Approximately 6.7 mm. Sepal texture: Densely pubescent with a mixture of glandular and nonglandular hairs. Gland color: Mixture of colorless, transparent; and 29C, transparent. Petal texture: Glabrous. Petal color: 159D with stripes of N66A.

*Corolla.*—Shape: Round. Diameter: Approximately 4.5 cm. Depth: Approximately 1.8 cm.

*Petals.*—Quantity: Approximately 6 petals and 1 irregularly-shaped petaloid per flower. Shape: Obovate. Appearance: Velvety, iridescent. Margin: Entire. Apex: Obtuse. Base: Attenuate. Length of upper petals: Approximately 2.8 cm. Width of upper petals: Approximately 2.0 cm. Length of lower petals: Approximately 2.6 cm. Width of lower petals: Approximately 2.0 cm. Texture of upper and lower surfaces: Glabrous. Color of upper surface of upper petals when fully open: N155B with a central spot of N57A transitioning to speckles of color toward margin and streaks of color at base. Color of lower surface of upper petals when fully open: N155A. Color of upper surface of lower petals when fully open: N155B with a central spot of N57C transitioning to speckles of color toward margin and irregular streaks of color at base. Color of lower surface of lower petals when fully open: N155B.

*Calyx.*—Shape: 5-pointed star. Diameter: Approximately 1.7 cm.

*Sepals.*—Quantity per flower: Approximately 5. Shape: Lanceolate. Margin: Entire. Apex: Acuminate. Base: Fused. Length of upper sepal: Approximately 1.0 cm. Width of upper sepal: Approximately 4.3 mm.

Length of lower sepals: Approximately 1.0 cm. Width of lower sepals: Approximately 2.4 mm. Texture of upper surface: Glabrous. Texture of lower surface: Densely pubescent with a mixture of glandular and nonglandular hairs. Gland color: Mixture of colorless, transparent; and 29C, transparent. Color of upper and lower surfaces: N144A.

*Pedicel.*—Strength: Strong. Aspect: Acute angle to stem. Length: Approximately 2.7 cm. Diameter: Approximately 1.0 mm. Texture: Densely glandular pubescent. Gland color: 29C, transparent. Color: 144A with overlay of 178B.

*Reproductive organs.*—Androecium: Quantity of mature stamens: Approximately 7 per flower. Anther shape: Oblong. Anther length: Approximately 2.0 mm. Anther color: 83A. Pollen amount: Moderate. Pollen color: N30D. Gynoecium: Pistil quantity: 1 per flower. Pistil length: Approximately 8.0 mm. Stigma shape: 5 branched. Stigma length: Approximately 3.0 mm. Stigma color: 54B. Style length: Approximately 2.0 mm. Style color: 54C. Ovary length: Approximately 3.0 mm. Ovary texture: Densely pubescent. Ovary color: N144A.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Baldeslipzle', substantially as herein shown and described.

* * * * *